United States Patent [19]

Weigand et al.

[11] Patent Number: 4,952,108

[45] Date of Patent: Aug. 28, 1990

[54] APPARATUS FOR AUTOMATICALLY FEEDING A SEQUENCE OF CRUCIBLES TO A TEST OVEN

[75] Inventors: Peter Weigand, Alzenau; Harald Langen, Babenhausen; Hans J. Kupka, Neuberg; Gerhard Rossel, Alzenau; Walter Weigand, Freigericht; Rudiger Wittenbeck, Hanau; Karl-Heinz Hessler, Mombris, all of Fed. Rep. of Germany

[73] Assignee: Foss Heraeus Analysensysteme GmbH, Hanau, Fed. Rep. of Germany

[21] Appl. No.: 307,360

[22] Filed: Feb. 6, 1989

[30] Foreign Application Priority Data

Feb. 20, 1988 [DE] Fed. Rep. of Germany ....... 3805321

[51] Int. Cl.$^5$ ............................................. B65G 25/00
[52] U.S. Cl. ........................................ 414/172; 294/90;
 414/222; 901/7; 198/468.6; 432/122
[58] Field of Search ............... 414/147, 150, 152, 153,
 414/172, 199, 222, 225, 226, 744.3; 901/7, 30;
 294/90; 198/468.6, 468.2; 432/122, 124;
 373/78, 138

[56] References Cited

U.S. PATENT DOCUMENTS

| | | | |
|---|---|---|---|
| 3,141,977 | 7/1964 | Fratantuno | 414/744.3 X |
| 4,072,253 | 2/1978 | Walters, Jr. | 414/189 X |
| 4,371,971 | 3/1983 | Bredeweg . | |
| 4,452,350 | 6/1984 | Shields | 414/222 X |
| 4,502,830 | 3/1985 | Inaba et al. | 414/744.3 X |
| 4,523,885 | 6/1985 | Bayne et al. | 414/156 |
| 4,569,218 | 2/1986 | Baker et al. | 414/223 |
| 4,610,628 | 9/1986 | Mizushina | 432/124 X |
| 4,626,203 | 12/1986 | Sakamoto | 414/153 X |
| 4,682,932 | 7/1987 | Yoshino | 414/744.3 |
| 4,770,590 | 9/1988 | Hugues et al. | 414/172 |
| 4,795,023 | 1/1989 | Gibbemeyer | 198/468.6 |

FOREIGN PATENT DOCUMENTS

| | | |
|---|---|---|
| 2427921 | 7/1975 | Fed. Rep. of Germany . |
| 3019466 | 3/1980 | Fed. Rep. of Germany . |
| 3540659 | 12/1986 | Fed. Rep. of Germany . |
| 53-129964 | 11/1978 | Japan ................................. 414/150 |

Primary Examiner—Robert J. Spar
Assistant Examiner—Robert S. Katz
Attorney, Agent, or Firm—Frishauf, Holtz, Goodman & Woodward

[57] ABSTRACT

The invention relates to an apparatus for automatically feeding each of a sequence of crucibles (3), which are arranged on a conveyor, to a test oven (12) for vaporization and content analysis of a sample contained in each crucible. For cradling each crucible, a gripper head (13) is provided. In order to provide an apparatus in which the number of mechanically moving parts is minimized, the gripper head is rigidly mounted on the end of an operating piston (7). The gripper head preferably comprises two spaced, co-linear crosspieces (16) which face each other and engage under an outwardly extending circumferential flange (17) on the top of each crucible (3). The operating piston (7) and a lifting piston (6) are oriented vertically and connected together at their tops by a transverse crossbar (10). Lifting piston (6) is rotated about its axis (8) by a drive motor, thereby revolving operating piston (7) along a circle (11). As operating piston (7) revolves, the gripper head (13) at its base engages under the flange (17) of a crucible on conveyor (1) at a transfer station (4). The pistons (6,7) rise together, lifting the crucible. Operating piston (7) revolves over the open upper end of a tubular oven (12), then lowers into it and closes with a collar element (20). Oven 12 vaporizes, by induction or the like, the sample and the vapors are analyzed. Then piston (7) rises and rotates to deposit the spent crucible and pick up another one.

16 Claims, 3 Drawing Sheets

APPARATUS FOR AUTOMATICALLY FEEDING A SEQUENCE OF CRUCIBLES TO A TEST OVEN

CROSS-REFERENCE TO RELATED PATENT DOCUMENTS

U.S. Pat. No. 4,371,971, BREDEWEG/LECO, SAMPLE LOADING MECHANISM, filed May 15, 1980 and issued Feb. 1, 1983.

German Patent Disclosure Document DE-OS No. 30 19 466, Vorrichtung zum Beschicken und Entladen des Induktionsofens einer Analysiereinrichtung mit Tiegeln, BREDEWEG et al./LECO CORP., filed May 21, 1980 and published Nov. 26, 1981;

German patent No. 24 27 921, BUNNIG/HERAEUS, issued Feb. 19, 1976;

German patent No. 35 40 659, KUPKA/HERAEUS, issued Jul. 16, 1987.

The present invention relates generally to automatic feeding of each of a sequence of sample-holding crucibles to the oven of an analysis device and, more particularly, to a system in which the crucibles are arranged in a conveyor and are sequentially lifted by a feeder into a cylindrical oven having a vertical axis, the feeder having a gripper with two claws for engaging each crucible.

BACKGROUND

German DE-OS No. 30 19 466 discloses a system for automatic feeding of crucibles to an oven of an analysis device and their removal therefrom. The device has an induction oven 14, 16 arranged above a conveyor 30. On the conveyor 30 are a plurality of crucibles 15, each containing a sample for analysis A gripper with movable claws or fingers 48, 50 is associated with each crucible 15. With these grippers, which are slidably arranged along a common rail 110 of the conveyor, slidable toward the axis of the oven, multiple crucibles 15 can be simultaneously gripped at their outer surfaces and moved in the direction of the oven axis. The respective crucible closest to the axis of the oven is placed under the oven onto a lifting piston 18, by means of which, after release of the gripper, the crucible can be introduced through an opening 22 (FIG. 1) into the oven above, specifically an induction oven as described.

After the analysis, the crucible is retracted from the oven and moved away. The grippers are pulled back along the rail into a position such that they grasp the arrayed crucibles individually, and, after movement of the rail in the direction of the oven, the crucibles advance one position, so that the next crucible is positioned under the oven. In order to open and close the grippers, a complicated mechanism, with a multiplicity of moving parts and springs, is necessary.

Analysis devices with a combustion apparatus for determining the content of one or more elements, such as C H O N (Carbon, Hydrogen, Oxygen, Nitrogen), in fluid or solid samples are widely known, for example as described in the above-noted German patents DE-PS No. 24 27 921 or DE-PS No. 35 40 659, assigned to the assignee of the present application.

THE INVENTION

It is an object of the present invention to improve on the above-noted prior art by devising an apparatus, for automatic, repeated feeding of crucibles to the oven of a sample-analysis device. The apparatus should distinguish itself by user-friendliness and breakdown resistance, and be limited to a minimum number of mechanically movable parts.

Briefly, the present invention features a gripper head, rigidly connected with one end of an operating piston or cylinder, and claws or fingers which are parallel crosspieces, each with an overhanging, rim, and which face each other. The operating piston or cylinder is connected with the end of a lifting piston, parallel to the latter's axis, via a crossbar to the end opposite the gripper head, in such a way that the gripper head is reciprocable into and out of the cylindrical oven and revolvable about the axis of the lifting piston.

An on- and off-loading or transfer station is located on the radius or circle of motion of the operating piston, to which station the crucibles are fed at intervals by the conveyor. The crucibles each have an outwardly protruding circumferential rim, under which the crosspieces of the gripper head engages. Mechanically movable parts are required merely for the reciprocation and rotation of the operating piston, on whose end the gripper head is located. The gripper head itself is securely fastened rigidly on the end of the operating piston. No moving gripper elements are needed for pickup or deposit of the crucibles. The gripper head is so shaped that it can engage under the outwardly extending circumferential flange of the respective crucibles, which are successively presented at the transfer station, with the gripper's claws, without the necessity to open or close the claws. All of the movement steps necessary for cradling and depositing of the crucible can be achieved by revolving the operating piston about the lifting piston and by axial reciprocation of the operating piston. For engagement of a crucible, the operating piston and its gripper head is revolved to the transfer station, where a crucible has been brought by the conveyor. The axial position of the operating piston is such that the inwardly extending edges of the claws are slightly spaced from the protruding flange of the crucible. The gripper head is revolved until the crucible is between the two claws of the gripper head. Then the operating piston is moved axially upward, so that the extending edges of the gripper head rest against the underside of the protruding flange of the crucible, and lift the crucible off the conveyor. The operating piston with the gripper head and the suspended crucible can now be revolved until the crucible is positioned over the oven tube, and can be lowered into it. In the oven tube, the crucible remains on the gripper head until the analysis process is concluded, i.e. until the sample contained in the crucible is fully vaporized or combusted. Thereafter, the operating piston is retracted out of the oven, the crucible is deposited back on the conveyor and the next crucible is advanced to the transfer station by the conveyor. The number of crucibles with samples which can be sequentially introduced into the oven is unlimited; the number can be varied as desired according to the length of the conveyor. The entire movement cycle of the lifting piston and of the operating piston with gripper head, which comprises only a few motions, can be easily automated using electrical and electronic regulation and control devices. For this purpose, it has been found to be advantageous to use as the lifting piston or to attach thereto, a worm-gear spindle which is driven by a stepper motor. On this spindle, a head or carriage on guide rods can be advanced, to which one secures the operating piston, via a crossbar. The individual lifting/lowering axial movements which the spindle must carry out can be specified by corresponding programming of the stepper motor controls.

Since the operating piston and the gripper head remain in the oven tube during the entire combustion process, which may reach 1100° C., these parts are preferably made of aluminum oxide which withstands such temperatures. In order to keep the oven tube sealed gas-tight during the combustion process, there is provided on the end of the operating piston, a collar or end element, above the gripper head. This end element, upon introduction of the operating piston into the oven, closes the oven without any further measures. Preferably, the spindle is driven by a stationary drive secured to the housing of the system, while the operating piston is revolved by a drive which travels axially, along with the lifting piston.

DRAWINGS

DETAILED DESCRIPTION

Figure 1:
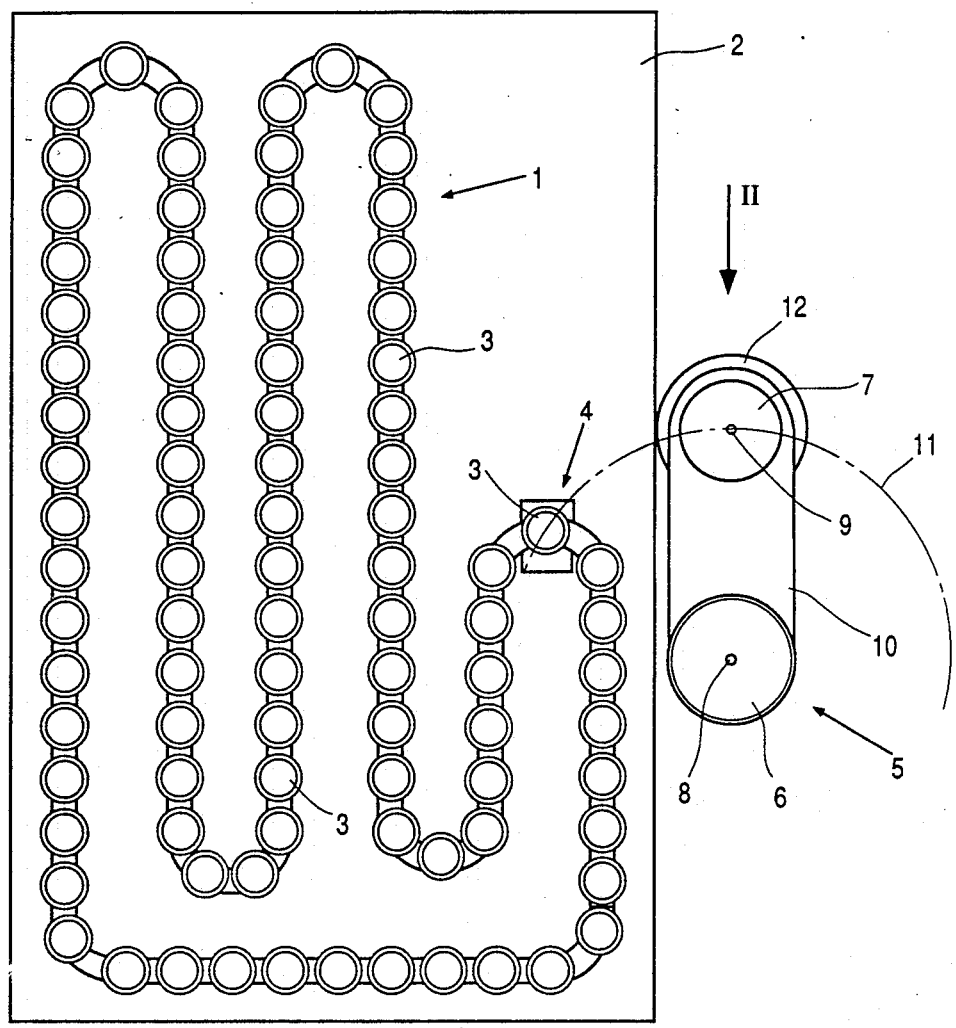
FIG. 1 is a top view of a sample-analysis device with a supply of crucibles.

The system has a conveyor 1, which extends endlessly in a meander across a worktable 2. On this conveyor are placed a plurality of crucibles 3. For the individual crucibles, once can provide, on the conveyor, receptacles (not shown), in order to fix the positions of the individual crucibles.

As shown in enlarged portion of FIG. 1, in the area of one of the inflections or U-turns of the conveyor meander, there is provided an on- and off-loading station 4, hereinafter referred to for the sake of brevity a's a transfer station, at which the crucibles containing the samples to be analyzed are taken off the conveyor 1. The feeding system 5 has a lifting piston 6 and an operating piston 7, whose respective axes are designated 8 and 9. Lifting piston 6, whose upper end is connected over a transverse (in this case horizontal) rod or crossbar 10 to the operating piston 7, as shown in FIG. 3, is axially movable as well as rotatable about axis 8, so that the radius of motion (shown as dash-dotted circle 11) of the operating piston 7, connected to lifting piston 6, crosses the on- and off-loading station 4. Along this travel circle 11 also lies a cylindrical oven 12, into which is introduced the respective crucible 3 containing the sample to be analyzed.

In order to position the individual crucibles at the on and off-loading station 4, one can provide an optical sensor such as a light beam or barrier across the conveying path (not shown) connected with the drive of conveyor 1.

Figure 4:
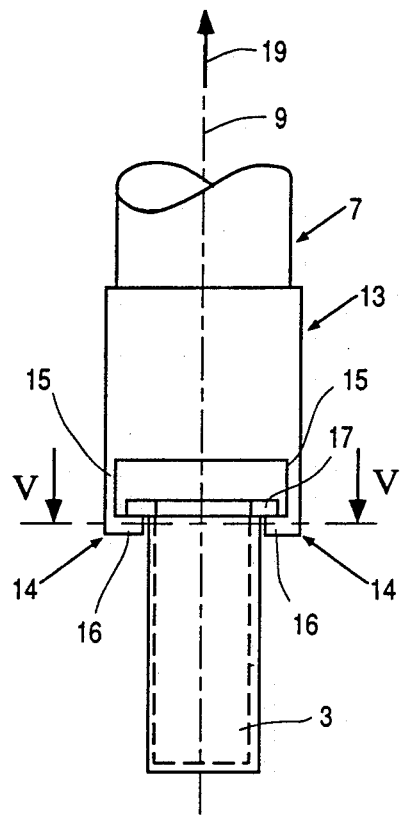
FIG. 4 shows a gripper head on the end of the operating piston with a crucible suspended therein.
Figure 5:
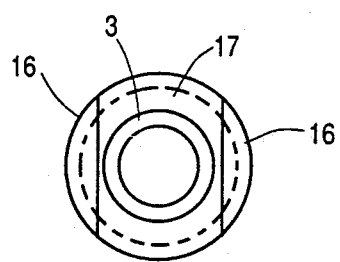
FIG. 5 is a sectional view taken along section line V—V of FIG. 4.

At the end of operating piston 7, which is preferably made of aluminum oxide, there is provided a gripper head 13, preferably also of aluminum oxide, which is detailed in FIGS. 4 and 5. Gripper head 13 has two claws 14, which each comprise a bar or strip 15 extending in the direction of axis 9 of operating piston 7 and a radially inwardly extending rim 16, which preferably runs from the piston-remote end of bar 15 toward central axis 9.

As shown in FIG. 5, the inner edge of each rim 16 may be a chord across the annular flange 17 at the top of each crucible 3. In each pair of claws 14, a crucible 3 is suspended by its radially outwardly protruding flange 17. The spacing of bars 15 is selected to be slightly larger than the radius of flange 17, so that this circumferential flange can be received between the pair of bars 15. Correspondingly, the length of the facing surfaces of the two overhanging rims 16 are selected such that the rims 16 form a secure seat for circumferential flange 17, while the radially smaller body of crucible 3 can be freely received between rims 16. To permit adaptation of the gripper head 13 to differing crucibles 3, it is releasably secured along a separation line 18 to operating piston 7. Since gripper head 13 is open on at least one side, as shown in FIG. 5, it can revolve underneath the circumferential rim 17 of a crucible 3 resting on its base and, by a subsequent lifting motion in the direction of arrow 19 of FIG. 4, engage the circumferential rim 17 of crucible 3 and lift the crucible. No parts on gripper head 13 need be moved to accomplish this engagement and lifting process.

Figures 2, 3:
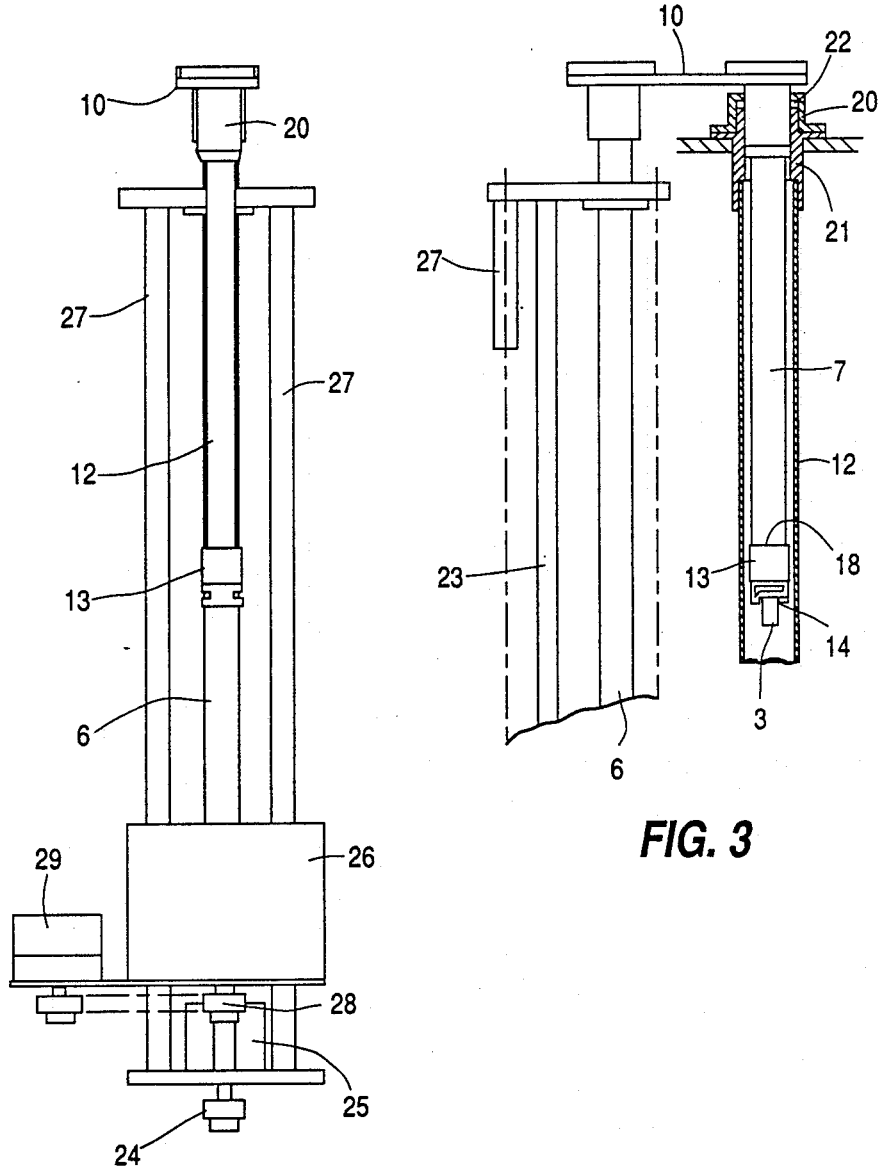
FIG. 2 is a side view of the loading device of FIG. 1, taken in the direction of arrow II thereof.
FIG. 3 is another side view, rotated 90° with respect to FIG. 2, showing an operating piston introduced into an oven tube.

After a crucible 3, as described above, has been engaged by gripper head 13 in the area of on- and off-loading station 4, lifting piston 6 is rotated on its axis 8 into the position shown in FIG. 1, above oven tube 12, and thereafter operating piston 7, together with the crucible 3 suspended in gripper head 13 attached thereto, is introduced into oven tube 12, as illustrated in FIG. 3. In order to close off oven tube 12 during the combustion process, an end element 20 is provided between the end of operating piston 7 and the crossbar 10 which connects lifting piston 6 and operating piston 7. End element 20 seals with an O-ring 22 against a closure element 21 of the oven tube 12.

For axial extension of lifting piston 6 and operating piston 7, a worm-gear spindle 23, is provided, which is rotatable by means of a drive motor 25 which engages a drive gear 24 as shown. Upon rotation of worm-gear spindle 23, a carriage 26, which rides on multiple guide rods 27, is displaced. Lifting piston 6 is formed as double concentric tubes. The inner one of these tubes is rotatable about its axis, in order to swing crossbar 10 and to revolve the operating piston 7 connected thereto. The rotation of this inner tube is driven via a further drive gear 28 by a further drive motor 29, which rests on and travels with carriage 26.

Various modifications are possible within the scope of the inventive concept.

We claim:

1. Apparatus for automatically feeding a sequence of crucibles (3) arranged on a conveyor (1) to a test oven (12), said crucibles each containing a sample, and being feedable by a vertical motion into a tubular oven (12), oriented with its longitudinal axis vertical, by a gripper head (13) with two claws (15) being used to cradle the crucible wherein, the gripper head (13) is rigidly secured to an end of an operating cylinder (7);

the claws (15) comprise two parallel-running crosspieces (15) each having an overhanging edge (16), the operating cylinder (7) has an end, remote from said gripper head (13), which is connected to an end of a parallel-oriented lifting cylinder (6) via transverse crossbar (10), said gripper head (13) being reciprocable into and out of said tubular oven (12) and revolvable about a longitudinal axis (8) of said lifting cylinder (6), an on- and off-loading station (4) located on a circle of motion (11) of said operating cylinder (7) about said longitudinal axis of said lifting cylinder (6);

said crucibles each having an outwardly extending circumferential flange (17), said crucibles being fed by said conveyor at intervals past said station (4), said crosspieces (15) of said gripper head (13) being so arranged that they engage under the circumferential flange (17) of the respective crucible.

2. Apparatus of claim 1, wherein said lifting cylinder is connected to a spindle (23).

3. Apparatus of claim 2, wherein said operating cylinder (7) and said gripper head (13) comprise aluminum oxide.

4. Apparatus of claim 3, further comprising a drive means (29) axially movable with said lifting cylinder (6) and operative to revolve said operating cylinder (7) about said longitudinal axis of said lifting cylinder (6).

5. Apparatus of claim 2, further comprising
an end element (20) on said operating cylinder (7) adjacent said crossbar (10), interfitting with and sealing said tubular oven (12).

6. Apparatus of claim 5, further comprising a drive means (29) axially movable with said lifting cylinder (6) and operative to revolve said operating cylinder (7) about said longitudinal axis of said lifting cylinder (6).

7. Apparatus of claim 2, further comprising a stationary drive motor (25) operative to vertically displace said lifting cylinder (7) to cause said reciprocal movement into and out of said oven.

8. Apparatus of claim 7, further comprising a drive means (29) axially movable with said lifting cylinder (6) and operative to revolve said operating cylinder (7) about said longitudinal axis of said cylinder (6).

9. Apparatus of claim 2, further comprising a drive means (29) axially movable with said lifting cylinder (6) and operative to revolve said operating cylinder (7) about said longitudinal axis of said lifting cylinder (6).

10. Apparatus of claim 1, wherein said operating cylinder (7) and said gripper head (13) comprise aluminum oxide.

11. Apparatus of claim 10, further comprising
an end element (20) on said operating cylinder (7) adjacent said crossbar (10), interfitting with said sealing said tubular oven (12).

12. Apparatus of claim 11, further comprising a drive means (29) axially movable with said lifting cylinder (6) and operative to revolve said operating cylinder (7) about said longitudinal axis of said lifting cylinder (6).

13. Apparatus of claim 10, further comprising a drive means (29) axially movable with said lifting cylinder (6) and operative to revolve said operating cylinder (7) about said longitudinal axis of said lifting cylinder (6).

14. Apparatus of claim 1, further comprising
an end element (20) on said operating cylinder (7) adjacent said crossbar (10), interfitting with and sealing said tubular oven (12).

15. Apparatus of claim 14, further comprising a drive means (29) axially movable with said lifting cylinder (6) and operative to revolve said operating cylinder (7) about said longitudinal axis of said lifting cylinder (6).

16. Apparatus of claim 1, further comprising a drive means (29) axially movable with said lifting cylinder (6) and operative to revolve said operating cylinder (7) about said longitudinal axis of said lifting cylinder (6).

* * * * *